(12) United States Patent
Vincent et al.

(10) Patent No.: US 9,382,170 B1
(45) Date of Patent: Jul. 5, 2016

(54) ALKYLATION PROCESS

(71) Applicant: ExxonMobil Chemical Patents Inc.

(72) Inventors: Matthew J. Vincent, Kingwood, TX (US); Vijay Nanda, Houston, TX (US); Terry E. Helton, Montgomery, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/981,379

(22) Filed: Dec. 28, 2015

Related U.S. Application Data

(63) Continuation of application No. 13/642,676, filed as application No. PCT/US2011/032661 on Apr. 15, 2011, now Pat. No. 9,249,067.

(60) Provisional application No. 61/346,763, filed on May 20, 2010.

(51) Int. Cl.
*C07C 2/66* (2006.01)

(52) U.S. Cl.
CPC ............... *C07C 2/66* (2013.01); *C07C 2529/08* (2013.01); *C07C 2529/70* (2013.01)

(58) Field of Classification Search
CPC .......................................................... C07C 2/66
USPC ......................................... 585/448, 449, 467
See application file for complete search history.

(56) References Cited

U.S. PATENT DOCUMENTS

| 4,185,040 A * | 1/1980 | Ward | B01J 29/08 502/64 |
| 2008/0058566 A1* | 3/2008 | Butler | B01J 29/06 585/448 |

* cited by examiner

*Primary Examiner* — Thuan D Dang
(74) *Attorney, Agent, or Firm* — Darryl M. Tyus

(57) ABSTRACT

The present invention provides an improved process for producing an alkylated aromatic compound from an at least partially untreated alkylatable aromatic compound having catalyst poisons and an alkylating agent, wherein said alkylatable aromatic compound stream is treated to reduce catalyst poisons with a treatment composition having a surface area/surface volume ratio of greater than or equal to 30 in$^{-1}$ (12 cm$^{-1}$) in a treatment zone separate from an alkylation reaction zone under treatment conditions including a temperature of from about 30° C. to about 300° C. to form an effluent comprising said treated alkylatable aromatic compound.

17 Claims, No Drawings

ALKYLATION PROCESS

CROSS-REFERENCE TO RELATED APPLICATIONS

This application is a continuation application of U.S. application Ser. No. 13/642,676, filed Jan. 7, 2013, now allowed, which is a National Stage Application of International Application No. PCT/US2011/032661, filed Apr. 15, 2011, which claims priority to and the benefits of U.S. Provisional patent application Ser. No. 61/346,763, filed May 20, 2010, the contents of which are fully incorporated by reference herein.

FIELD

The present invention relates to an improved process for producing an alkylated aromatic compound from an at least partially untreated alkylatable aromatic compound stream and an alkylating agent, wherein said at least partially alkylatable aromatic compound stream contains catalyst poisons which are at least partially removed by contacting with a treatment composition. In particular, this invention relates to processes to produce ethylbenzene, cumene and sec-butylbenzene from benzene streams which contain catalyst poisons which are at least partially removed by contacting with treatment composition which are preferably porous crystalline materials.

BACKGROUND

Of the alkylaromatic compounds advantageously produced by the present improved process, ethylbenzene and cumene, for example, are valuable commodity chemicals which are used industrially for the production of styrene monomer and coproduction of phenol and acetone respectively. In fact, a common route for the production of phenol comprises a process which involves alkylation of benzene with propylene to produce cumene, followed by oxidation of the cumene to the corresponding hydroperoxide, and then cleavage of the hydroperoxide to produce equimolar amounts of phenol and acetone. Ethylbenzene may be produced by a number of different chemical processes. One process which has achieved a significant degree of commercial success is vapor phase alkylation of benzene with ethylene in the presence of a solid, acidic ZSM-5 zeolite catalyst. Examples of such ethylbenzene production processes are described in U.S. Pat. No. 3,751,504 (Keown), U.S. Pat. No. 4,547,605 (Kresge) and U.S. Pat. No. 4,016,218 (Haag). U.S. Pat. No. 5,003,119 (Sardina) describes the use of zeolites X, Y, L, Beta, ZSM-5, Omega, and mordenite and chabazite in synthesis of ethylbenzene. U.S. Pat. No. 5,959,168 (van der Aalst) describes the use of zeolites Y, Beta, MCM-22, MCM-36, MCM-49 and MCM-56 in synthesis of ethylbenzene in a plant designed for use of aluminum chloride-based catalyst.

Another process which has achieved significant commercial success is liquid phase alkylation for producing ethylbenzene from benzene and ethylene since it operates at a lower temperature than the vapor phase counterpart and hence tends to result in lower yields of by-products. For example, U.S. Pat. No. 4,891,458 (Innes) describes the liquid phase synthesis of ethylbenzene with zeolite beta, whereas U.S. Pat. No. 5,334,795 (Chu) describes the use of MCM-22 in the liquid phase synthesis of ethylbenzene; and U.S. Pat. No. 7,649,122 (Clark) describes the use of MCM-22 in the liquid phase synthesis of ethylbenzene in the presence of a maintained water content. U.S. Pat. No. 4,549,426 (Inwood) describes the liquid phase synthesis of alkylbenzene with steam stabilized zeolite Y. U.S. Patent Publication No. 2009/0234169 A1 (Pelati) describes the liquid phase aromatic alkylation over at least one catalyst bed containing a first catalyst modified by inclusion of a rare earth metal ion.

Cumene has been produced commercially by the liquid phase alkylation of benzene with propylene over a Friedel-Craft catalyst, particularly solid phosphoric acid or aluminum chloride. Zeolite-based catalyst systems have been found to be more active and selective for propylation of benzene to cumene. For example, U.S. Pat. No. 4,992,606 (Kushnerick) describes the use of MCM-22 in the liquid phase alkylation of benzene with propylene.

Other publications show use of catalysts comprising crystalline zeolites for conversion of feedstock comprising an alkylatable aromatic compound and an alkylating agent to alkylaromatic conversion product under at least partial liquid phase conversion conditions. These include U.S. 2005/0197517A1 (Cheng); U.S. 2002/0137977A1 (Hendrickson); and U.S. 2004/0138051A1 (Shan) showing use of a catalyst comprising a microporous zeolite embedded in a mesoporous support; WO 2006/002805 (Spano); and U.S. Pat. No. 6,376,730 (Jan) showing use of layered catalyst; EP 0847802B1; and U.S. Pat. No. 5,600,050 (Huang) showing use of catalyst comprising 30 to 70 wt. % H-Beta zeolite, 0.5 to 10 wt. % halogen, and the remainder alumina binder.

Other such publications include U.S. Pat. No. 5,600,048 (Cheng) describing preparing ethylbenzene by liquid phase alkylation over acidic solid oxide such as MCM-22, MCM-49 and MCM-56, Beta, X, Y or mordenite; U.S. Pat. No. 7,411,101 (Chen) describing preparing ethylbenzene or cumene by liquid phase alkylation over acidic solid oxide such as PSH-3, ITQ-2, MCM-22, MCM-36, MCM-49, MCM-56, and Beta at conversion conditions including a temperature as high as 482° C. and pressure as high as 13,788 kPa; and U.S. Pat. No. 7,645,913 (Clark) describing preparing alkylaromatic compounds by liquid phase alkylation in a multistage reaction system over acidic solid oxide catalyst in the first reaction zone having more acid sites per unit volume of catalyst than the catalyst in the second reaction zone at conversion conditions including for ethylbenzene a temperature as high as 270° C. and pressure as high as 8,300 kPa, and for cumene a temperature as high as 250° C. and pressure as high as 5,000 kPa. U.S. Patent Publication No. 2008/0287720 A1 (Clark) describes alkylation of benzene over catalyst of MCM-22 family material in a reaction zone having water content maintained at from 1 to 900 wppm. U.S. Patent Publication No. 2009/0137855 A1 (Clark) describes a mixed phase process for producing alkylaromatic compounds from a dilute alkene feedstock which also includes alkane impurities. In the latter publication, the volume ratio of liquid to vapor in the feedstock is from 0.1 to 10.

A problem common to processes using zeolites, for example, alkylation processes for producing alkylaromatic compounds, such as ethylbenzene and cumene, is reduced operational life of the catalyst because of deactivation caused by various catalyst poisons present in the feedstock to the processes. First step guard beds or separation zones containing poison adsorbents such as clay, resins, molecular sieves and the like may be employed to limit such poisons in the feedstock. Such feedstock includes, but is not limited to, an alkylatable aromatic feedstock, such as a benzene feedstock. Examples of publications showing this include U.S. Pat. No. 6,894,201 B1 (Schmidt) using clay, molecular sieve or resin adsorbents; U.S. Pat. No. 5,744,686 (Gajda) using a non-acidic molecular sieve having a silica/alumina ratio in excess of 100 and an average pore size less than 5.5 Angstroms such as zeolite 4A and ZSM-5; and U.S. Patent Publication No.

2005/0143612 A1 (Hwang) using distillation, extraction or adsorption over acidic clay, zeolite, activated alumina, activated carbon, silica gel, and ion exchange resin. Feedstock pretreatment is also shown in U.S. Pat. No. 7,199,275 B2 (Smith) involving contact with a first molecular sieve having a Si/Al molar ratio less than 5, e.g., 13X, followed by contact with a second molecular sieve having a Si/Al molar ratio of greater than 5, e.g., 4A; and in U.S. Patent Publication No. 2009/0259084 A1 (Smith) involving contact with a first molecular sieve comprising zeolite X, followed by contact with a second molecular sieve comprising zeolite Y.

In WO98/07673 (Samson), a process of preparing an alkylated benzene or mixture of alkylated benzenes involving contacting a benzene feedstock with a solid acid, such as an acidic clay or acid zeolite, in a pretreatment zone at a temperature greater than about 130° C. but less than about 300° C. to form a pretreated benzene feedstock, and thereafter contacting the pretreated benzene feedstock with (a) an alkylating agent in an alkylation zone or (b) a transalkylating agent in a transalkylation zone, in the presence of an alkylation/transalkylation catalyst so as to prepare the alkylated benzene or mixture of alkylated benzenes. The pretreatment step is said to improve the lifetime of the alkylation/transalkylation catalyst. Preferred products are ethylbenzene and cumene.

A single alkylation reaction zone containing catalyst having surface area to volume ratios within prescribed ranges is shown in U.S. Pat. No. 6,888,037 B2 (Dandekar) where cumene is manufactured in the liquid phase over catalyst having surface area/volume of 80 to 200 in$^{-1}$ (31 to 79 cm$^{-1}$), preferably from 100 to 150 in$^{-1}$ (39 to 59 cm$^{-1}$). A single reaction zone is shown in an alkylation process in U.S. Pat. No. 7,816,574 B2 (Clark) wherein the catalyst therein is a particulate material of from 125 to 790 microns in size with a surface area/volume of greater than 79 in$^{-1}$ (31 cm$^{-1}$). U.S. Pat. No. 5,118,896 (Steigelmann) shows an aromatic alkylation process using a single alkylation reaction zone, i.e., a catalytic distillation reactor, with catalyst having a pore volume of 0.25 to 0.50 cc/g and pores having a radius greater than 450 Angstroms and a catalyst particle diameter of not more than 1/32 inch (0.08 cm). U.S. Pat. No. 4,185,040 (Ward) shows an aromatic alkylation process using a single alkylation reaction zone with zeolite Y catalyst having a ratio of external surface area/volume of 85 to 160 in$^{-1}$ (34 to 63 cm$^{-1}$).

U.S. Patent Publication No. 2009/0306446 A1 (Clark) shows a process for producing monoalkylated aromatics in a single reaction zone having two different catalysts, the first catalyst having a surface area/volume ratio greater than 79 cm$^{-1}$, and a second catalyst comprising particles having a surface area/volume between 78 and 79 cm$^{-1}$.

Existing alkylation processes for producing alkylaromatic compounds, for example, ethylbenzene and cumene, inherently produce polyalkylated species as well as the desired monoalkyated product. It is therefore normal to transalkylate the polyalkylated species with additional aromatic feed, for example benzene, to produce additional monoalkylated product, for example ethylbenzene or cumene, either by recycling the polyalkylated species to the alkylation reactor or, more frequently, by feeding the polyalkylated species to a separate transalkylation reactor. Examples of catalysts which have been used in the alkylation of aromatic species, such as alkylation of benzene with ethylene or propylene, and in the transalkylation of polyalkylated species, such as polyethylbenzenes and polyisopropylbenzenes, are listed in U.S. Pat. No. 5,557,024 (Cheng) and include MCM-49, MCM-22, PSH-3, SSZ-25, zeolite X, zeolite Y, zeolite Beta, acid dealuminized mordenite and TEA-mordenite. Transalkylation over a small crystal (<0.5 micron) form of TEA-mordenite is also disclosed in U.S. Pat. No. 6,984,764.

Where the alkylation step is performed in the liquid phase, it is also desirable to conduct the transalkylation step under liquid phase conditions. However, by operating at relatively low temperatures, liquid phase processes impose increased requirements on the catalyst, particularly in the transalkylation step where the bulky polyalkylated species must be converted to additional monoalkylated product without producing unwanted by-products. This has proven to be a significant problem in the case of cumene production where existing catalysts have either lacked the desired activity or have resulted in the production of significant quantities of by-products such as ethylbenzene and n-propylbenzene.

Although it is suggested in the art that catalysts for conversion of feedstock comprising an alkylatable aromatic compound and an alkylating agent to alkylaromatic conversion product under at least partial liquid phase conversion conditions are composed of a porous crystalline material, e.g., aluminosilicate molecular sieves, having an MWW framework structure type, the present improved process has not been taught. Finding a commercially acceptable method for such processes conducted under at least partial liquid phase conversion conditions which delays alkylation catalyst deactivation and does not negatively affect monoselectivity, i.e., lower di- or polyalkyl product make, would allow capacity expansion in existing plants and lower capital expense for grassroots plants.

According to the present invention, an improved process was unexpectedly discovered for producing an alkylated aromatic compound from an at least partially untreated alkylatable aromatic compound stream and an alkylating agent, wherein said alkylatable aromatic compound stream contains catalyst poisons which are at least partially removed by contacting with a treatment composition. This is especially the case when the process is to produce ethylbenzene, cumene and sec-butylbenzene from benzene streams which contain catalyst poisons which are at least partially removed by contacting with treatment composition which are preferably porous crystalline materials.

SUMMARY

According to the present invention, there is provided an improved process for producing an alkylated aromatic compound stream from an at least partially untreated alkylatable aromatic compound stream having catalyst poisons and an alkylating agent stream. Preferably, the alkylated aromatic compound is a monoalkylated aromatic compound such as ethylbenzene, cumene and sec-butylbenzene; preferably, the alkylatable aromatic compound is benzene; and preferably, the alkylating agent is ethylene, propylene or butene. The untreated alkylatable aromatic compound stream is treated with a treatment composition having a high surface area/volume ratio and in the presence of the alkylating agent in order to reduce catalyst poisons.

One embodiment of the process of this invention comprises the steps of: (a) contacting an at least partially untreated alkylatable aromatic compound stream having said catalyst poisons and an alkylating agent stream with a treatment composition in a treatment zone separate from, and preferably upstream from, an alkylation reaction zone under treatment conditions to remove at least a portion of said catalyst poisons and to alkyate at least a portion of said alkylatable aromatic compound to form a treated effluent stream which comprises treated alkylatable aromatic compound, an alkylated aromatic compound and a reduced amount of catalyst poisons, wherein said treatment composition has a surface area/surface volume ratio of greater than 30 in$^{-1}$ (12 cm$^{-1}$), said treatment conditions include a temperature of from about 30° C. (ambient) to about 300° C. and a pressure from about 101 kPa (ambient) to about 4601 kPa, and a molar ratio of untreated alkylatable aromatic compound to alkylating agent of greater than or equal to about 25:1; and (b) contacting said treated alkylatable aromatic compound in said effluent stream and additional said alkylating agent stream with a catalyst composition in said alkylation reaction zone separate from, and preferably downstream from, said treatment zone under at least partial liquid phase catalytic conversion conditions to form an alkylated effluent stream which comprises additional alkylated aromatic compound, wherein said catalyst composition comprises a porous crystalline material having a framework structure type selected from the group consisting of FAU, *BEA, MOR, MWW and mixtures thereof, wherein said at least partial liquid phase catalytic conversion conditions include a temperature of from about 100° C. to about 300° C., a pressure from about 689 kPa to about 4601 kPa, a molar ratio of treated alkylatable aromatic compound to alkylating agent of from about 0.01:1 to about 25:1, and a feed weight hourly space velocity (WHSV) based on alkylating agent of from about 0.5 to about 500 hr$^{-1}$.

DETAILED DESCRIPTION OF THE INVENTION

Definitions

As used herein, the term "alkylatable aromatic compound" means a compound that may receive an alkyl group and an "alkylating agent" is a compound which may donate an alkyl group.

The term "aromatic" in reference to the alkylatable aromatic compounds which may be useful as feedstock herein is to be understood in accordance with its art-recognized scope. This includes alkyl substituted and unsubstituted mono- and polynuclear compounds. Compounds of an aromatic character that possess a heteroatom are also useful provided they do not act as catalyst poisons under the reaction conditions selected.

The term "catalyst poisons" means an impurity present in the at least partially untreated alkylatable aromatic compound stream, particularly the benzene stream, which comprise one or more compounds which contain at least one of the following elements: nitrogen, halogens, oxygen, sulfur, arsenic, selenium, tellurium, phosphorus, and Group 1 through Group 12 metals.

As used herein, the term "liquid or partial liquid phase" in reference to the present improved process means that the reaction mixture comprises greater than or equal to 10 volume percent liquid, for example greater than or equal to 30 volume percent liquid, up to 100 volume percent liquid.

As used herein, the term "surface area/surface volume ratio" means the ratio obtained by dividing the surface area of the formulated particle by the geometric surface volume of the formulated particle. As used herein, the term "geometric surface volume" means the volume of the formulated particle calculated as though the particle is a solid particle without regard to the volume of any pores, channels or chambers on the surface or inside of the formulated particle. For example, for a geometric sphere, the surface area/surface volume ratio (S/V) is 3/r, where r is the radius of the particle.

As used herein, the term "untreated alkylatable aromatic compound" means a stream which contains an alkylatable aromatic compound and any catalyst poisons before it is contacted with the treatment composition of this invention.

For the avoidance of doubt, such untreated alkylatable aromatic compound may have been subjected to other treatment steps in upstream or downstream processes in which at least a portion of catalyst poisons may have been removed, such that there are remaining catalyst poisons for removal by the process of this invention.

As used herein, the term "wppm" means parts-per-million by weight.

Treatment Composition

In one or more embodiments, the treatment composition for use in the present improved process comprises preferably a porous crystalline material and has a surface area/surface volume ratio of greater than or equal to 30 in$^{-1}$ (12 cm$^{-1}$); or a surface area/surface volume ratio of greater than or equal to 50 in$^{-1}$ (20 cm$^{-1}$); or a surface area/surface volume ratio of greater than or equal to 75 in$^{-1}$ (30 cm$^{-1}$); or a surface area/surface volume ratio of greater than or equal to 125 in$^{-1}$ (50 cm$^{-1}$); or a surface area/surface volume ratio of greater than or equal to 250 in$^{-1}$ (99 cm$^{-1}$); or a surface area/surface volume ratio of greater than or equal to 500 in$^{-1}$ (197 cm$^{-1}$).

The surface area/surface volume ratio of the treatment composition is in the range of greater than or equal to 30 in$^{-1}$ (12 cm$^{-1}$) to less than or equal to 70 in$^{-1}$ (28 cm$^{-1}$); or in the range of greater than or equal to 75 in$^{-1}$ (30 cm$^{-1}$) to less than or equal to 125 in$^{-1}$ (49 cm$^{-1}$); or in the range of greater than or equal to 125 in$^{-1}$ (49 cm$^{-1}$) to less than or equal to 250 in$^{-1}$ (98 cm$^{-1}$); or in the range of greater than or equal to 250 in$^{-1}$ (98 cm$^{-1}$) to less than or equal to 500 in$^{-1}$ (197 cm$^{-1}$); or in the range of 70 in$^{-1}$ (28 cm$^{-1}$) to 100 in$^{-1}$ (39 cm$^{-1}$); or in the range of 180 in$^{-1}$ (71 cm$^{-1}$) to 220 in$^{-1}$ (87 cm$^{-1}$); or in the range of 600 in$^{-1}$ (236 cm$^{-1}$) to 770 in$^{-1}$ (303 cm$^{-1}$).

The method of making the treatment composition having the desired surface area/surface volume ratio is not particularly limited. One or more of the long-known techniques, such as spray drying, prilling, pelletizing and extrusion, have been and are being used to produce macrostructures in the form of, for example, spherical particles, extrudates, pellets and tablets. A summary of these techniques is described in *Catalyst Manufacture* by A. B. Stiles and T. A. Koch, Marcel Dekker, New York, 1995.

The treatment composition having the desired surface area/surface volume ratio may be made, for example, by controlling its particle size (i.e., crushed particles).

The treatment composition having the desired surface area/surface volume ratio may also be made, for example, by using a shaped treatment composition. Non-limiting examples of shaped treatment compositions, include hollow or solid polylobal extrudates made by extrusion as described in U.S. Pat. No. 4,441,990 (Huang); hollow shaped extrudates as described in U.S. Pat. No. 7,198,845 (Van Hasselt); longitudinally channeled cylindrical extrudates as described in U.S. Pat. No. 4,432,643 (Kyan); grooved cylindrical extrudates as described in U.S. Pat. No. 4,328,130.

For example, a cylindrically-shaped treatment composition having a diameter of 1/32 inch (0.08 cm) and a length of 3/32 inch (0.24 cm) has a surface area/surface volume ratio of 141 in$^{-1}$ (56 cm$^{-1}$). A treatment composition as a quadralobal solid extrudate having the external shape disclosed in FIG. 4 of U.S. Pat. No. 4,441,990 and having a maximum cross-sectional dimension of 1/16 inch (0.16 cm) and a length of 3/16 inch (0.48 cm) has a surface area/surface volume ratio of 128 in$^{-1}$ (50 cm$^{-1}$). A treatment composition as a hollow tubular extrudate having an external diameter of 1/10 inch (0.25 cm), an internal diameter of 1/30 inch (0.08 cm) and a length of 3/10 inch (0.75 cm) has a surface area/surface volume ratio of 136 in$^{-1}$ (54 cm$^{-1}$).

The surface area/volume ratio may be determined by measuring a physical dimension and the curvature of the treatment composition particle, and then calculating the surface area and volume based on known equations of geometry.

The treatment compositions of this invention may comprise one or a mixture of molecular sieves, and must have any particle shapes or configuration to allow for the required surface area/surface volume ratio.

The treatment composition as porous crystalline molecular sieves may have, as non-limiting examples, the structure of *BEA, including zeolite Beta (described in U.S. Pat. No. 3,308,069); the structure of FAU, including faujasite, zeolite Y, Ultrastable Y (USY, described in U.S. Pat. Nos. 3,293,192 and 3,449,070), Dealuminized Y (Deal Y, preparation of which is described in U.S. Pat. No. 3,442,795), rare earth exchanged Y (REY, described in U.S. Pat. No. 4,415,438), Ultrahydrophobic Y (UHP-Y, described in U.S. Pat. No. 4,401,556); the structure of MOR, including mordenite (a naturally occurring material), and TEA-mordenite (a synthetic mordenite prepared from a reaction mixture comprising a tetraethylammonium directing agent, disclosed in U.S. Pat. Nos. 3,766,093 and 3,894,104). The treatment composition may include mixtures of the above porous crystalline molecular sieves. Other suitable porous crystalline molecular sieves include, but are not limited to, ZSM-3, ZSM-4, ZSM-5, ZSM-14, ZSM-18, and ZSM-20, including mixtures thereof.

In one or more embodiments, the treatment composition may also be selected from the group consisting of clay, resin, solid phosphoric acid, activated alumina, Linde type X, such as 13X, a Linde type A, such as 4A or 5A. and mixtures thereof, as non-limiting examples.

A summary of the molecular sieves and/or zeolites, in terms of production, modification and characterization of molecular sieves, is described in *Molecular Sieves-Principles of Synthesis and Identification* by R. Szostak, Blackie Academic & Professional, London, 1998, Second Edition. In addition to molecular sieves, amorphous materials, chiefly silica, aluminum silicate and aluminum oxide, have been used as adsorbents and catalyst supports.

Catalytic Composition

The catalytic composition suitable for use in the present invention comprises a porous crystalline material having a framework structure type selected from the group consisting of FAU, *BEA, MOR, MWW and mixtures thereof, preferably MWW framework structure.

Porous crystalline materials having a FAU framework structure type include faujasite, zeolite Y, Ultrastable Y (USY), Dealuminized Y (Deal Y), Rare Earth Y (REY), Ultrahydrophobic Y (UHP-Y), described above, or mixtures thereof.

A porous crystalline material having a *BEA framework structure type is zeolite beta, described above.

A porous crystalline materials having a MOR framework structure type is mordenite, TEA-mordenite, described above, or a mixture thereof.

Porous crystalline materials having MWW framework structure type generally have an X-ray diffraction pattern including d-spacing maxima at 12.4±0.25, 6.9±0.15, 3.57±0.07 and 3.42±0.07 Angstroms. The X-ray diffraction data used to characterize the material are obtained by standard techniques using the K-alpha doublet of copper as the incident radiation and a diffractometer equipped with a scintillation counter and associated computer as the collection system.

Examples of MWW framework structure type materials include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in U.S. Pat. No. 6,231,751), ITQ-30 (described in WO 2005-118476), MCM-36 (described in U.S. Pat. No. 5,250,277), MCM-49 (described in U.S. Pat. No. 5,236,575), MCM-56 (described in U.S. Pat. No. 5,362,697) and UZM-8 (described in U.S. Pat. No. 6,756,030).

Preferably, the catalytic composition comprising a porous crystalline material having MWW framework structure type is PSH-3, SSZ-25, ERB-1, ITQ-1, ITQ-2, ITQ-30, MCM-22, MCM-36, MCM-49, MCM-56, UZM-8, EMM-10, EMM-12, EMM-13 or mixtures thereof.

In an embodiment of the invention, the catalyst will have a Relative Activity measured as an $RA_{220}$ of at least 8.6, for example from 8.6 to 12.0, or $RA_{180}$ of at least 3.5, for example from 3.5 to 6.0.

Methods for producing the catalysts required for use in the present invention comprise those taught in the publications listed herein and incorporated herein by reference. For example, U.S. Pat. No. 4,954,325 describes crystalline MCM-22 and catalyst comprising same, U.S. Pat. No. 5,236,575 describes crystalline MCM-49 and catalyst comprising same, and U.S. Pat. No. 5,362,697 describes crystalline MCM-56 and catalyst comprising same.

Binders

The catalyst composition and treatment composition for use in the present invention may include an inorganic oxide matrix material or binder. Such matrix or binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful matrix or binder materials employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

For the improvement of the present invention, relative proportions of the crystalline molecular sieve and binder or matrix are not especially critical.

The catalyst for use in the present invention, or its crystalline molecular sieve component, may or may not contain added functionalization, such as, for example, a metal of Group VI (e.g., Cr and Mo), Group VII (e.g., Mn and Re) or Group VIII (e.g., Co, Ni, Pd and Pt), or phosphorus.

Alkylatable Aromatics, Alkylating Agents and Products

Alkylatable aromatic compounds suitable for the present invention include substituted aromatic compounds that can be alkylated must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction.

Suitable alkylatable aromatic compounds include benzene, naphthalene, anthracene, naphthacene, perylene, coronene, and phenanthrene, with benzene being preferred.

Generally the alkyl groups that can be present as substituents on the aromatic compound contain from 1 to about 22 carbon atoms and usually from about 1 to 8 carbon atoms, and most usually from about 1 to 4 carbon atoms.

Suitable alkylatable aromatics compounds include alkyl substituted aromatic compounds include toluene, xylene, isopropylbenzene, n-propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic compounds can also be used as starting materials and include aromatic organics such as are produced by the alkylation of aromatic organics with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing a mixture of benzene, toluene and/or xylene constitutes a useful feed for the processes of this invention.

Suitable alkylating agents for the present invention include olefins such as ethylene and propylene; alcohols (inclusive of monoalcohols, dialcohols, trialcohols, etc.) such as methanol, ethanol and the propanols; aldehydes such as formaldehyde, acetaldehyde and propionaldehyde; and alkyl halides such as methyl chloride, ethyl chloride and the propyl chlorides, and so forth.

Mixtures of light olefins are useful as alkylating agents in the alkylation process of this invention. Accordingly, mixtures of ethylene and propylene which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
| --- | --- | --- |
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Non-limiting examples of reaction products that may be obtained from the process of the present invention include ethylbenzene from the reaction of benzene with ethylene, cumene from the reaction of benzene with propylene, ethyltoluene from the reaction of toluene with ethylene and cymenes from the reaction of toluene with propylene. Particularly preferred process mechanisms of the invention relate to the production of cumene by the alkylation of benzene with propylene, and production of ethylbenzene by the alkylation of benzene with ethylene.

The reactants for the present improved process can be in partially or completely liquid phase and can be neat, i.e., free from intentional admixture or dilution with other material, or they can be brought into contact with the required catalyst composition with the aid of carrier gases or diluents such as, for example, hydrogen or nitrogen.

Catalyst Poisons and Treatment Process

The at least partially untreated alkylatable aromatic compound stream may contain impurities which can act over time to poison the catalytic composition. These catalyst poisons may comprise up to about 10 wppm, or up to 5 wppm, or up to 1 wppm, or up to 0.5 wppm, or up to about 0.1 wppm of said at least partially untreated alkylatable aromatic compound stream. Such catalyst poison may be in the range from at least 1 wppm to 5 wppm, or 1 wppm to 10 wppm, or even 5 wppm to 10 wppm by weight of said at least partially untreated alkylatable aromatic compound stream. Such catalyst poisons comprise one or more compounds which contain at least one of the following elements: nitrogen, halogens, oxygen, sulfur, arsenic, selenium, tellurium, phosphorus, and Group 1 through Group 12 metals.

In the present invention, the at least partially untreated alkylatable aromatic compound stream having catalyst poisons is treated by contacting this stream and an alkylating agent stream with a treatment composition in a treatment zone separate from and upstream from an alkylation reaction zone. The contacting is performed under treatment conditions to remove at least a portion of said catalyst poisons and to alkylate at least a portion of said alkylatable aromatic compound, thereby forming a treated effluent stream which comprises a treated alkylatable aromatic compound as well as small amount of an alkylated aromatic compound and a reduced amount of catalyst poisons. As noted above, the treatment composition comprises a porous crystalline zeolite having a high surface area/surface volume ratio.

In one or more embodiments, the treatment conditions include a temperature of from about 30° C. (ambient) to about 300° C., from about 100° C. to 200° C., or from about 100° C. to 125° C. The treatment pressure is from about 101 kPa (ambient) to about 4601 kPa, from about 101 kPa to about 3000 kPa, and from about 101 kPa to about 2500 kPa. The treatment weight hourly space velocity (WHSV) is in the range from about 5 to 70 hr$^{-1}$, preferably 12 to 45 hr$^{-1}$, based on the weight of the at least partially untreated alkylatable aromatic compound.

The treatment composition has the capacity to absorb greater than about 100, or greater than about 300, or greater than about 500, or greater than about 700, or greater than about 900 micromoles of collidine per gram of treatment composition. The capacity to absorb collidine is in the range from about 50 up to about 150, from about 150 to about 300, from about 300 to about 500, from about 500 to about 700, from about 700 to about 900, from about 900 to about 1000 micromoles of collidine per gram of treatment composition.

The treatment composition has the capacity to absorb greater than about 900, or greater than about 1500, or greater than about 2500, or greater than about 3500, or greater than about 5500 wppm N-formyl morpholine (NFM) based on the weight of the treatment composition. The capacity to absorb NFM is in the range from about 900 up to about 1500, from about 1500 to about 2500, from about 2500 to about 3500, from about 3500 to about 5500, from about 5500 to about 7000 wppm NFM based on the weight of the treatment composition.

In operation, the at least partially untreated alkylatable aromatic stream having said catalyst poisons is fed to the treatment zone along with the alkylating agent stream. This untreated alkylatable aromatic compound mixture is contacted with the treatment composition in a treatment zone separate from an alkylation reaction zone under treatment conditions to remove at least a portion of said catalyst poisons and to alkylate at least a portion of said alkylatable aromatic compound to form a treated effluent stream which comprises treated alkylatable aromatic compound, an alkylated aromatic compound and a reduced amount of catalyst poisons, wherein said treatment composition has a surface area/surface volume ratio of greater than 30 $in^{-1}$ (12 $cm^{-1}$), said treatment conditions include a temperature of from about 30° C. to about 300° C. and a pressure from about 101 kPa to about 4601 kPa, and a molar ratio of untreated alkylatable aromatic compound to alkylating agent of greater than or equal to about 25:1. In the treatment zone, at least one catalyst poison is absorbed by and strongly bound to the treatment composition causing it to be at least partially removed from the at least partially untreated alkylatable aromatic compound stream.

The high surface area/volume ratio of the treatment composition and the high ratio of the at least partially untreated alkylatable aromatic compound to alkylating agent (particularly as compared to the catalytic conversion conditions employed in alkylation reactions) provide substantially improved removal of catalyst poisons from the untreated alkylatable aromatic compound stream in the treatment zone. Moreover, such catalyst poison removal is further combined at the same time with alkylating at least a portion of said alkylatable aromatic compound to produce the desired alkylated aromatic compound.

In the treatment zone, the molar ratio of the at least partially untreated alkylatable aromatic compound to alkylating agent of greater than or equal to about 10:1; or greater than or equal to about 25:1; or greater than or equal to about 50:1; or greater than or equal to about 75:1; or greater than or equal to about 100:1. The molar ratio of the at least partially untreated alkylatable aromatic compound to alkylating agent is in the range of 10:1 to 25:1, or 25:1 to 50:1, or 50:1 to 75:1; or 75:1 to 100:1. In some embodiments, the ratio of at least partially untreated alkylatable aromatic to alkylating agent is in the range of 5:1 to 50:1 for a single bed of treatment composition in the treatment zone.

As a result of the treatment step of the present invention by contacting the at least partially untreated alkylatable aromatic compound stream with the treatment composition under the aforementioned treatment conditions, at least 1 wt. %, at least 5 wt. %, at least 10 wt. %, at least 15 wt. %, at least 25 wt. %, at least 50 wt. %, at least 75 wt. %, or up to at least 99 wt. % of said catalyst poisons in the at least partially untreated alkylatable aromatic compound stream are removed.

In addition, as supplied, most commercial at least partially untreated alkylatable aromatic compound streams are water saturated, and may contain up to about 50 wppm, generally up to about 200 wppm, water. The present process provides an advantageous method of reducing the amounts of theses catalyst poisons in commercial at least partially untreated alkylatable aromatic compound streams to acceptable levels having aforementioned amounts of water.

Alkylation Process

In the process of this invention, the physical apparatus used for the treatment zone and that for the alkylation reaction zone may be, for example, separated and in series whereby the effluent from the treatment zone is then recovered and fed to the downstream reaction zone. Also, the same apparatus may be used for both the treatment zone and the alkylation reaction zone so long as all alkylatable aromatic compound contacts the treatment composition in the treatment zone at the treatment conditions before effluent comprising the treated alkylatable aromatic compound contacts the alkylation catalyst at alkylation conversion conditions in the separate portion of the reaction zone. In the latter situation, of course, the effluent from the treatment zone of step (a) above comprising treated alkylatable aromatic compound and any unreacted alkylating agent would pass directly to the alkylation reaction zone of step (b) above.

The improved alkylation process of this invention may be conducted such that the reactants, i.e., the effluent from the treatment zone comprising treated alkylatable aromatic compound are brought into contact with the catalytic composition in a suitable reaction zone such as, for example, in a flow reactor containing a fixed bed of the catalyst composition, under effective catalytic conversion conditions. Preferably, at least partial liquid phase catalytic conversion conditions which include a temperature of from about 100° C. to about 300° C., preferably from about 100° C. to about 285° C., most preferably from about 100° C. to about 200° C., a pressure of from about 689 to about 4601 kPa, preferably from about 689 to about 3102 kPa, a molar ratio of treated alkylatable aromatic compound to alkylating agent of from about 0.1:1 to about 25:1, preferably from about 0.5:1 to about 10:1, and a feed weight hourly space velocity (WHSV) based on the alkylating agent of from about 0.1 to 500 $hr^{-1}$, preferably from about 0.5 to about 100 $hr^{-1}$.

When the treated alkylatable aromatic compound comprises treated benzene and the alkylating agent is ethylene to produce ethylbenzene, the alkylation reaction is preferably carried out under at least partial liquid phase catalytic conversion conditions including a temperature of from about 100° C. to about 280° C., from about 100° C. to about 230° C., preferably from about 125° C. to about 260° C.; a pressure up to about 4601 kPa, preferably from about 689 kPa to about 3102 kPa; a weight hourly space velocity (WHSV) based on the ethylene alkylating agent of from about 0.1 to about 20 $hr^{-1}$, preferably from about 0.5 to about 6 $hr^{-1}$; and a ratio of treated benzene to ethylene in the alkylation reaction zone of from about 0.1:1 to about 30:1 molar, preferably from about 1:1 to about 20:1 molar.

When the treated alkylatable aromatic compound comprises treated benzene and the alkylating agent is propylene to produce cumene, the reaction may also take place under at least partial liquid phase catalytic conversion conditions including a temperature of less than about 200° C., from about 100 to about 200° C., from about 125° C. to about 180° C.; a pressure of about 3102 kPa or less, e.g., from about 1724 kPa to about 3102 kPa; a weight hourly space velocity (WHSV) based on propylene alkylating agent of from about 0.1 $hr^{-1}$ to about 25 $hr^{-1}$, preferably from about 0.3 $hr^{-1}$ to about 5 $hr^{-1}$; and a molar ratio of treated benzene to propylene in the alkylation reactor of from about 0.1:1 to about 30:1, more preferably from about 1:1 to about 20:1 molar.

In the reaction mechanism of the present invention, the alkylation reactor effluent may contain excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the distillation may be further distilled to separate monoalkylated product from polyalkylated products and other heavies.

The polyalkylated products separated from the alkylation reactor effluent may be reacted with additional aromatic feed in a transalkylation reactor, separate from the alkylation reactor, over a suitable transalkylation catalyst. The transalkylation catalyst may comprise one or a mixture of crystalline molecular sieves having the structure of zeolite Beta, zeolite Y, mordenite or an MWW framework structure type material, described above.

Relative Activity

The catalytic composition for use in the present invention may have a Relative Activity measured as an $RA_{220}$ of at least 8.6, for example from 8.6 to 12.0, or $RA_{180}$ of at least 3.5, for example from 3.5 to 6.0, allowing operation at lower reaction pressures, e.g. a reactor outlet pressure of about 3102 kPa or less, and lower alkylating agent, e.g. ethylene or propylene, feed supply pressure of 3102 kPa or less, e.g. 2758 kPa or less. As used herein, the Relative Activity measured as $RA_{220}$ or $RA_{180}$ is determined by a method similar to that described by S. Folger in *Elements of Chemical Reactor Engineering, 2$^{nd}$ Edition*, pages 406-407. In this method using an adiabatic reactor, an energy balance is used to relate the temperature rise to the conversion of ethylene. With thermocouple positions, inlet temperature, pressure and conversions known, the Relative Activity of the catalyst may be determined using a differential reactor analysis. For this analysis, the Relative Activity is calculated by the percent temperature rise divided by the percentage of the bed length. In short, Relative Activity (RA)=ΔT/L, wherein ΔT is percent temperature rise and L is percentage of the bed length. When inlet temperature to the adiabatic reactor is 180° C., the value of RA is $RA_{180}$ and when inlet temperature to the adiabatic reactor is 220° C., the value of RA is $RA_{220}$.

This RA determination is exemplified by the following experiments in which an adiabatic ¾" pipe reactor with multipoint thermocouples is loaded with approximately 28 grams of a specified catalyst. The catalyst is tightly packed between inert alumina beds to provide good flow distribution. A feed comprising ethylene and benzene (1:1.5 molar), heated to an inlet temperature of 180 or 220° C., passes through the bed of catalyst enabling reaction and exits the reactor as effluent. A part of the effluent is recycled back to the feed in order to maintain an adiabatic temperature rise of approximately 40° C. The recycle to feed (weight) ratio is maintained at 6 to 1 to maintain liquid phase conditions. The multipoint thermocouple in the bed consists of six thermocouples that are used to measure the temperature at 6 points inside the bed. Results are described in the following table with Catalyst A and B being the same MWW structure material.

| Catalyst | Inlet Temperature (° C.) | Thermocouple Position (Percentage of Bed) | Percent Temperature Rise | RA |
|---|---|---|---|---|
| B (Lower Activity) | 180 | 4.9% | 9.0% | 1.8 |
| B (Lower Activity) | 220 | 4.9% | 32% | 6.5 |
| A (Higher Activity) | 180 | 4.4% | 23% | 5.2 |
| A (Higher Activity) | 220 | 4.4% | 47% | 10.7 |

EXAMPLES

Non-limiting examples of the invention involving an improved alkylation mechanism are described with reference to the following experiments. In these experiments, two separate beds, a treatment zone and an alkylation reaction zone are placed in series. The first bed (treatment zone) containing a particular treatment composition is used for treatment of benzene containing nitrogen compounds (catalyst poisons) to protect a downstream alkylation reaction zone capable of doing alkylation reaction chemistry. The benzene is fed to the treatment zone along with ethylene. The effluent of the treatment zone is then mixed with ethylene and fed to the alkylation reaction zone containing alkylation catalyst. The number of days of stable alkylation operation (run length) is determined from when deactivation is first observed to occur in the alkylation reaction zone. Deactivation of catalyst in the alkylation reaction zone thus correlates to the run length of the treatment composition and its apparent capacity (at constant flow conditions). Once the treatment composition no longer retains poisons (slippage), it needs to either be regenerated or replaced. Examples 1-4 below demonstrate the efficacy of treatment compositions comprising the surface area/surface volume ratio required of the materials to be used herein. The poison capacities of the treatment compositions in the treatment zones are calculated from the time on stream and the time at which catalyst deactivation is observed in the alkylation reaction zone.

The surface area/surface volume ratio was determined by using an optical process to measure particle dimensions and particle curvature using the Advanced Laboratory Imaging and Analysis System (ALIAS) obtained from Cascade Data Systems of Wilsonville, Oreg.

Example 1

A 16 gram quantity of material formulated as ¹/₂₀ inch (0.13 cm) quadrulobe particles comprising MCM-49 (which has MWW framework structure) was placed in both the treatment zone (as a treatment composition) and the alkylation reaction zone (as a catalytic composition). The quadrulobe material had a surface area/surface volume ratio of approximately 180-220 in$^{-1}$ (71-87 cm$^{-1}$). Benzene comprising 0.3 wppm of Nitrogen (hereinafter referred to as "N") in the form of N-formylmorphaline and ethylene were fed to the treatment zone at ambient pressure, a benzene/ethylene molar ratio between 50:1 and 70:1, approximately 60:1, a WHSV of approximately 21 hr$^{-1}$ on a benzene basis and 180° C. (liquid phase). The effluent from the treatment zone, mixed with ethylene, was then fed to the alkylation reaction zone maintained at a temperature of 180° C., with the mixture in the liquid phase, benzene/ethylene molar ratio of 18:1, and with a WHSV of 0.77 hr$^{-1}$ based on ethylene. The catalytic composition in the reaction zone did not deactivate for 5 to 7 days. Therefore, the poison capacity of the treatment composition in the treatment zone was calculated to be approximately 900-1000 wppm of N.

Example 2

A 16 gram quantity of material formulated as ¹/₂₀ inch (0.13 cm) quadrulobe particles comprising MCM-49 (which has MWW framework structure), crushed to 200-250 micron-sized particles, was placed in the treatment zone (as a treatment composition), and a 28 gram quantity of material formulated as ¹/₂₀ inch (0.13 cm) quadrulobe particles comprising MCM-49 was placed in the alkylation reaction zone (as a catalytic composition). The crushed material in the treatment zone (treatment composition) had a surface area/surface volume ratio of approximately 600-770 in$^{-1}$ (236-303 cm$^{-1}$). The quadrulobe material in the alkylation reaction zone (catalytic composition) had a surface area/surface volume ratio of approximately 180-220 in$^{-1}$ (71-87 cm$^{-1}$). Benzene comprising 0.3 wppm of N in the form of N-formylmorphaline and ethylene were fed to the treatment zone at ambient pressure, a benzene/ethylene molar ratio between 9:1 and 26:1, a WHSV of approximately 20 hr$^{-1}$ based on benzene and 180° C. (liquid phase). The effluent from the treatment zone, mixed with ethylene, was then fed to the reaction zone maintained at a temperature of 220° C. with the mixture in the liquid phase, the benzene/ethylene molar ratio of approximately 20:1, and with a WHSV of approximately 0.85 hr$^{-1}$ based on ethylene. The catalytic composition in the reaction zone did not deactivate for 8 to 9 days. Therefore, the poison capacity of the treatment composition in the treatment zone was calculated to be approximately 1200 wppm of nitrogen (N).

Example 3

A 16 gram quantity of treatment composition comprising zeolite Beta (which has *BEA framework structure) formulated as ¹⁄₂₀ inch (0.13 cm) quadrulobe particles with a surface area/surface volume ratio of 180-220 in$^{-1}$ (71-87 cm$^{-1}$) was placed in the treatment zone, and a 28 gram quantity of material formulated as ¹⁄₂₀ inch (0.13 cm) quadrulobe particles comprising MCM-49 was placed in the alkylation reaction zone. Benzene comprising 0.3 wppm of N in the form of N-formylmorphaline and ethylene was fed to the treatment zone at ambient pressure, a benzene/ethylene molar ratio of approximately 55:1, a WHSV of 21 hr$^{-1}$ based on benzene and 180° C. (liquid phase). (However the selectivity of the treatment composition was very poor, producing approximately 2.5 to 4.0 times the amount of diethylbenzene as an MWW catalyst.) The effluent from the treatment zone, mixed with ethylene, was then fed to the reaction zone maintained at a temperature of 180° C., with the mixture in the liquid phase, a benzene/ethylene molar ratio of 18:1, and with a WHSV of approximately 0.77 hr$^{-1}$ based on benzene. The catalytic composition in the reaction zone did not deactivate for 38-42 days. Therefore, the poison capacity of the treatment composition in the treatment zone was calculated to be approximately 5950 wppm of N.

Example 4

A 16 gram quantity of treatment composition comprising faujasite (which has FAU framework structure) formulated as ¹⁄₁₆ inch (0.16 cm) cylinder particles with a surface area/surface volume ratio of a surface area/surface volume ratio of 70-100 in$^{-1}$ (28-39 cm$^{-1}$) was placed in the treatment zone (as a treatment composition), and a 28 gram quantity of material formulated as ¹⁄₂₀ inch (0.13 cm) quadrulobe particles comprising an MWW catalyst was placed in the alkylation reaction zone (as a catalytic composition). Benzene comprising 0.3 wppm of N in the form of N-formylmorphaline and ethylene were fed to the treatment zone at ambient pressure, a benzene/ethylene molar ratio of approximately 75:1, a WHSV of 21 hr$^{-1}$ based on benzene and 170° C. (liquid phase). (However, the selectivity of the treatment composition was very poor, producing approximately 5.0 times the amount of diethylbenzenes as an MWW catalyst). The effluent from the treatment zone, mixed with ethylene, was then fed to the reaction zone maintained at a temperature of 220° C., with the mixture in the liquid phase, benzene/ethylene molar ratio of 18:1, and with a WHSV of approximately 0.85 hr$^{-1}$ based on benzene. The catalytic composition in the reaction zone did not deactivate for 13-15 days. Therefore, the poison capacity of the treatment composition in the treatment zone was calculated to be approximately 2000 wppm of N.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended heretobe limited to the examples and descriptions set forth herein but rather that the claims be construed as encompassing all the features of patentable novelty which reside in the present invention, including all features which would be treated as equivalents thereof by those skilled in the art to which the invention pertains.

The invention claimed is:

1. A process for producing an alkylated aromatic compound stream from at least one partially untreated alkylatable aromatic compound stream having catalyst poisons comprising a compound having nitrogen as an element, the process comprising the steps of:
   (a) feeding said untreated alkylatable aromatic compound stream having said catalyst poisons and a portion of an alkylating agent stream in the liquid phase to a treatment zone having a treatment composition comprising a zeolite having a FAU framework type;
   (b) contacting said untreated alkylatable aromatic compound stream and said alkylating agent stream with said treatment composition in said treatment zone separate from an alkylation reaction zone under liquid phase treatment conditions to remove at least a portion of said catalyst poisons and to alkylate at least a portion of said alkylatable aromatic compound to form a treated effluent stream which comprises treated alkylatable aromatic compound, an alkylated aromatic compound and a reduced amount of catalyst poisons, wherein said treatment composition has a surface area/surface volume ratio in the range of 180 in$^{-1}$ (71 cm$^{-1}$) to 220 in$^{-1}$ (87 cm$^{-1}$) and absorbs at least 2000 wppm nitrogen compounds, said liquid phase treatment conditions include a temperature of from about 30° C. to about 300° C. and a pressure from about 101 kPa to about 4601 kPa, and a molar ratio of untreated alkylatable aromatic compound to alkylating agent of greater than or equal to about 75:1; and
   (c) contacting said treated alkylatable aromatic compound in said effluent stream and an additional portion of said alkylating agent stream with a catalyst composition in said alkylation reaction zone separate from said treatment zone under at least partial liquid phase catalytic conversion conditions to form an alkylated effluent stream which comprises additional alkylated aromatic compound, wherein said catalyst composition comprises a porous crystalline material having a framework structure type selected from the group consisting of FAU, *BEA, MOR, MWW and mixtures thereof, wherein said at least partial liquid phase catalytic conversion conditions include a temperature of from about 100° C. to about 300° C., a pressure from about 689 kPa to about 4601 kPa, a molar ratio of treated alkylatable aromatic compound to alkylating agent of from about 0.01:1 to about 25:1, and a feed weight hourly space velocity (WHSV) based on alkylating agent of from about 0.5 to about 500 hr$^{-1}$.

2. The process of claim 1, wherein said porous crystalline material having said FAU framework structure type is faujasite, zeolite Y, Ultrastable Y (USY), Dealuminized Y (Deal Y), Rare Earth Y (REY), Ultrahydrophobic Y (UHP-Y) or a mixture thereof.

3. The process of claim 1, wherein said porous crystalline material having said *BEA framework structure type is zeolite beta.

4. The process of claim 1, wherein said porous crystalline material having said MOR framework structure type is mordenite, TEA-mordenite or a mixture thereof.

5. The process of claim 1, wherein said porous crystalline material having said MWW framework structure type has an X-ray diffraction pattern including d-spacing maxima at 12.4±0.25, 6.9±0.15, 3.57±0.07 and 3.42±0.07 Angstroms in as-synthesized or calcined form.

6. The process of claim 1, wherein said porous crystalline material having MWW framework structure type is PSH-3, SSZ-25, ERB-1, ITQ-1, ITQ-2, ITQ-30, MCM-22, MCM-36, MCM-49, MCM-56, UZM-8, EMM-10, EMM-12, EMM-13 or mixtures thereof.

7. The process of claim 1, wherein said alkylatable aromatic compound is selected from the group consisting of benzene, naphthalene, anthracene, naphthacene, perylene, coronene, phenanthrene and mixtures thereof.

8. The process of claim 1, wherein said alkylatable aromatic compound is benzene, said alkylating agent is ethylene and said alkylated aromatic compound is ethylbenzene.

9. The process of claim 1, wherein said alkylatable aromatic compound is benzene, said alkylating agent is propylene and said alkylated aromatic compound is cumene.

10. The process of claim 1, wherein said alkylatable aromatic compound is benzene, said alkylating agent is butene and said alkylated aromatic compound is sec-butylbenzene.

11. The process of claim 1, wherein said alkylatable aromatic compound is benzene, said alkylating agent is ethylene, said alkylated aromatic compound is ethylbenzene, and said at least partial liquid phase conversion conditions include a temperature of from about 100° C. to about 280° C., a pressure of about 3102 kPa or less, a weight hourly space velocity (WHSV) based on the ethylene of from about 0.1 to about 20 hr$^{-1}$, and a ratio of benzene to ethylene in the alkylation reactor of from about 0.5:1 to about 20:1 molar.

12. The process of claim 11, wherein said porous crystalline material having said MWW framework structure type has an X-ray diffraction pattern including d-spacing maxima at 12.4±0.25, 6.9±0.15, 3.57±0.07 and 3.42±0.07 Angstroms.

13. The process of claim 11, wherein said porous crystalline material having MWW framework structure type is PSH-3, SSZ-25, ERB-1, ITQ-1, ITQ-2, ITQ-30, MCM-22, MCM-36, MCM-49, MCM-56, UZM-8, EMM-10, EMM-12, EMM-13 or mixtures thereof.

14. The process of claim 1, wherein said alkylatable aromatic compound comprises benzene, said alkylating agent is propylene, said alkylated aromatic compound comprises cumene, and said at least partial liquid phase conversion conditions include a temperature of less than about 200° C., a pressure of about 3102 kPa or less, a weight hourly space velocity (WHSV) based on propylene alkylating agent of from about 0.1 hr$^{-1}$ to about 250 hr$^{-1}$, and a ratio of benzene to propylene in the alkylation reactor of from about 0.5:1 to about 20:1 molar.

15. The process of claim 14, wherein said porous crystalline material having said MWW framework structure type has an X-ray diffraction pattern including d-spacing maxima at 12.4±0.25, 6.9±0.15, 3.57±0.07 and 3.42±0.07 Angstroms.

16. The process of claim 14, wherein said porous crystalline material having MWW framework structure type is PSH-3, SSZ-25, ERB-1, ITQ-1, ITQ-2, ITQ-30, MCM-22, MCM-36, MCM-49, MCM-56, UZM-8, EMM-10, EMM-12, EMM-13 or mixtures thereof.

17. The process of claim 1, wherein said treatment conditions of contacting step (a) includes a treatment weight hourly space velocity (WHSV) based on the untreated alkylatable aromatic compound in the range from about 5 to 70 hr$^{-1}$.

\* \* \* \* \*